United States Patent
Georgilis et al.

(10) Patent No.: US 11,628,264 B2
(45) Date of Patent: Apr. 18, 2023

(54) ENDOTRACHEAL TUBE WITH RESISTANT MATERIAL, SLEEVE AND CUFF

(71) Applicant: BRYAN MEDICAL, INC., Cincinnati, OH (US)

(72) Inventors: Andrew J. Georgilis, Cincinnati, OH (US); Bill Depel, Crown Point, IN (US)

(73) Assignee: Bryan Medical Inc., Cincinnati, OH (US)

(*) Notice: Subject to any disclaimer, the term of this patent is extended or adjusted under 35 U.S.C. 154(b) by 327 days.

(21) Appl. No.: 16/874,723

(22) Filed: May 15, 2020

(65) Prior Publication Data

US 2021/0030984 A1 Feb. 4, 2021

Related U.S. Application Data (60) Provisional application No. 62/850,784, filed on May 21, 2019.

(51) Int. Cl.
*A61M 16/04* (2006.01)

(52) U.S. Cl.
CPC .... *A61M 16/0422* (2014.02); *A61M 16/0434* (2013.01); *A61M 2205/15* (2013.01); *A61M 2207/00* (2013.01)

(58) Field of Classification Search
CPC .......... A61M 16/0422; A61M 16/0434; A61M 16/0459; A61M 16/0475; A61M 16/0486
See application file for complete search history.

(56) References Cited

U.S. PATENT DOCUMENTS

| | | | | |
|---|---|---|---|---|
| 3,884,242 A | * | 5/1975 | Bazell | A61M 25/008 128/207.14 |
| 4,327,721 A | * | 5/1982 | Goldin | A61M 16/0486 128/207.15 |
| 4,335,723 A | * | 6/1982 | Patel | A61M 25/10 604/920 |
| 4,834,087 A | | 5/1989 | Coleman et al. | |
| 4,976,261 A | | 12/1990 | Gluck et al. | |
| 5,065,757 A | * | 11/1991 | Dragisic | A61M 16/0447 128/207.14 |
| 5,103,816 A | | 4/1992 | Kirschbaum et al. | |
| 5,139,019 A | * | 8/1992 | Smith | A61M 16/04 128/207.14 |
| 5,190,810 A | * | 3/1993 | Kirschbaum | G21F 1/125 428/920 |
| 5,311,863 A | * | 5/1994 | Toppses | F16L 11/12 128/207.14 |
| 5,469,864 A | * | 11/1995 | Rosenblatt | A61B 90/04 128/207.14 |
| 5,499,625 A | | 3/1996 | Frass et al. | |

(Continued)

OTHER PUBLICATIONS

International Search Report and Written Opinion for International Application No. PCT/US2020/033130; 15 pages, dated Aug. 12, 2020.

*Primary Examiner* — Kathryn E Ditmer (74) *Attorney, Agent, or Firm* — Taft Stettinius & Hollister LLP; Ryan O. White; Derek B. Lavender (57) ABSTRACT

A tube for delivering fluid that has a tube extending between a first opening and a second opening, an expandable cuff formed on a distal end of the tube, a resistant member formed around a portion of the tube, and a sleeve formed around the resistant member. Wherein, the sleeve presents a substantially smooth outer surface.

21 Claims, 9 Drawing Sheets

(56) References Cited

U.S. PATENT DOCUMENTS

| | | | |
|---|---|---|---|
| 5,749,357 A | 5/1998 | Linder | |
| 5,881,726 A * | 3/1999 | Neame | A61M 16/0445 |
| | | | 128/207.14 |
| 6,374,827 B1 | 4/2002 | Bowden et al. | |
| 2005/0284483 A1* | 12/2005 | Patel | A61M 16/0486 |
| | | | 128/207.14 |

* cited by examiner

ENDOTRACHEAL TUBE WITH RESISTANT MATERIAL, SLEEVE AND CUFF

CROSS REFERENCE TO RELATED APPLICATIONS

The present disclosure claims the benefit of U.S. Provisional Application No. 62/850,784 filed on May 21, 2019, the contents of which are incorporated herein in their entirety.

FIELD OF THE DISCLOSURE

The present disclosure relates to an endotracheal tube, and more specifically to an endotracheal tube that has a resistant layer.

BACKGROUND

Often during medical procedures such as surgeries and the like the physician desires to control the flow of fluids to and from the patient. In one such example, an endotracheal tube is utilized to control the flow of fluid to the patient's lungs. As part of the insertion process, the endotracheal tube is passed through the patient's mouth, past the vocal chords, and partially into the trachea. The endotracheal tube often has an inflatable cuff on a distal end that can be selectively inflated to provide a fluid seal between the distal end of the endotracheal tube and the surrounding walls of the trachea. The inflated cuff fluidly seals the endotracheal tube to the trachea walls to allow the endotracheal tube to provide a fluid channel with which the physician can control the volume and type of fluid entering and leaving the patient's lungs.

The fluid introduced through the endotracheal tube is often gaseous and includes oxygen to ensure the patients lungs are supplied sufficient oxygen during the procedure. Further, many procedures involve operating on soft tissue around the trachea or other portion of the patient's anatomy that is proximate to the endotracheal tube. In these procedures, the physician must take special care to ensure the endotracheal tube is not compromised with the cutting device. Further still, many procedures involve using a surgical laser or other heat-generating device as the cutting device.

Some endotracheal tubes are made of a fire-resistant material around the outside of the endotracheal tube. While this may aid in preventing the endotracheal tube from being compromised by the heat-generating cutting device, the exterior surface is abrasive to the patient's soft tissue. More specifically, as the endotracheal tube is positioned within, and removed from, the patient's trachea it will pass over the vocal chords among other things. Accordingly, the abrasive exterior of the conventional fire-resistance endotracheal tube often causes undue trauma to the soft tissue of the patient during insertion and extraction.

SUMMARY

One embodiment is a tube for delivering fluid that has a tube extending between a first opening and a second opening, an expandable cuff formed on a distal end of the tube, a resistant member formed around a portion of the tube, and a sleeve formed around the resistant member. Wherein, the sleeve presents a substantially smooth outer surface.

One example of this embodiment has a second expandable cuff formed at the distal end of the tube. Further, this example has a first inflation lumen that is fluidly coupleable to the expandable cuff, the first inflation lumen being partially formed within a wall of the tube. This example may also have a second inflation lumen that is fluidly coupleable to the second expandable cuff, the second inflation lumen being partially formed within the wall of the tube. In one aspect of this example, the first inflation lumen and the second inflation lumen are not fluidly coupled to one another in the wall of the tube.

In yet another example, the resistant member is formed from a material that resists penetration by a laser. In one aspect of this example, the resistant member is formed of an aluminum material. In yet another example the resistant member is wrapped around at least a portion of the tube. In one aspect of this example, the sleeve is positioned radially outside of the resistant member and extends at least the length of the resistant member.

In another example of this embodiment, adhesive is applied to the proximal and distal end of the resistant member and the sleeve to couple the resistant member and the sleeve to the tube. In one example, the sleeve is formed of silicon.

Another embodiment is an endotracheal tube assembly that has an airway tube forming a fluid channel from a first opening to a second opening and defining a tube wall, a resistant member formed around a portion of the airway tube, a sleeve formed around the resistant member, and a first cuff formed along the airway tube proximate to the second opening. Wherein, the resistant member is formed around the airway tube and the sleeve is formed of a single material having a substantially smooth outer surface.

One example of this embodiment has a second cuff formed along the airway adjacent to the first cuff. One aspect of this example includes a first inflation lumen fluid channel defined at least partially within the tube wall and fluidly coupled to the first cuff and a second inflation lumen fluid channel defined at least partially within the tube wall and fluidly coupled to the second cuff. In one aspect of this example, the first cuff and second cuff are inflatable independent of one another. In yet another aspect, the resistant member is positioned radially inside of at least a portion of the first cuff.

In another example of this embodiment, the resistant material is wrapped around the airway tube and the sleeve radially compresses the resistant material towards the airway tube. In another aspect of this example, the resistant material and the sleeve are adhesively coupled to the airway tube at a proximal and a distal end.

Another embodiment includes a method for manufacturing an endotracheal tube that includes forming an airway tube with at least two inflation lumen passageways defined in a wall of the airway tube, winding a resistant member around an outer portion of the airway tube, expanding a sleeve and positioning the sleeve around the resistant member, allowing the sleeve to contract to thereby compress the resistant member against the airway tube, and coupling a proximal and distal cuff to the airway tube and fluidly coupling a different one of the two inflation lumen passageways to each of the proximal and distal cuffs.

One example of this embodiment includes applying adhesive to a proximal and distal end of both the sleeve and resistant member to thereby adhesively couple the sleeve and resistant member to the airway tube.

BRIEF DESCRIPTION OF THE DRAWINGS

The above-mentioned aspects of the present disclosure and the manner of obtaining them will become more apparent and the disclosure itself will be better understood by reference to the following description of the embodiments of the disclosure, taken in conjunction with the accompanying drawings, wherein:

FIG. 8 is a partial sectional view of one cuff of the endotracheal tube assembly of FIG. 6a; and FIG. 9 is a method for fluidly coupling a cuff to a lumen for the endotracheal tube assembly of FIG. 6a.

Corresponding reference numerals are used to indicate corresponding parts throughout the several views.

DETAILED DESCRIPTION

For the purposes of promoting an understanding of the principles of the present disclosure, reference will now be made to the embodiments described herein and illustrated in the drawings and specific language will be used to describe the same. It will nevertheless be understood that no limitation of the scope of the present disclosure is thereby intended, such alterations and further modifications in the illustrated devices and methods, and such further applications of the principles of the present disclosure as illustrated therein being contemplated as would normally occur to one skilled in the art to which the present disclosure relates.

Figure 1:
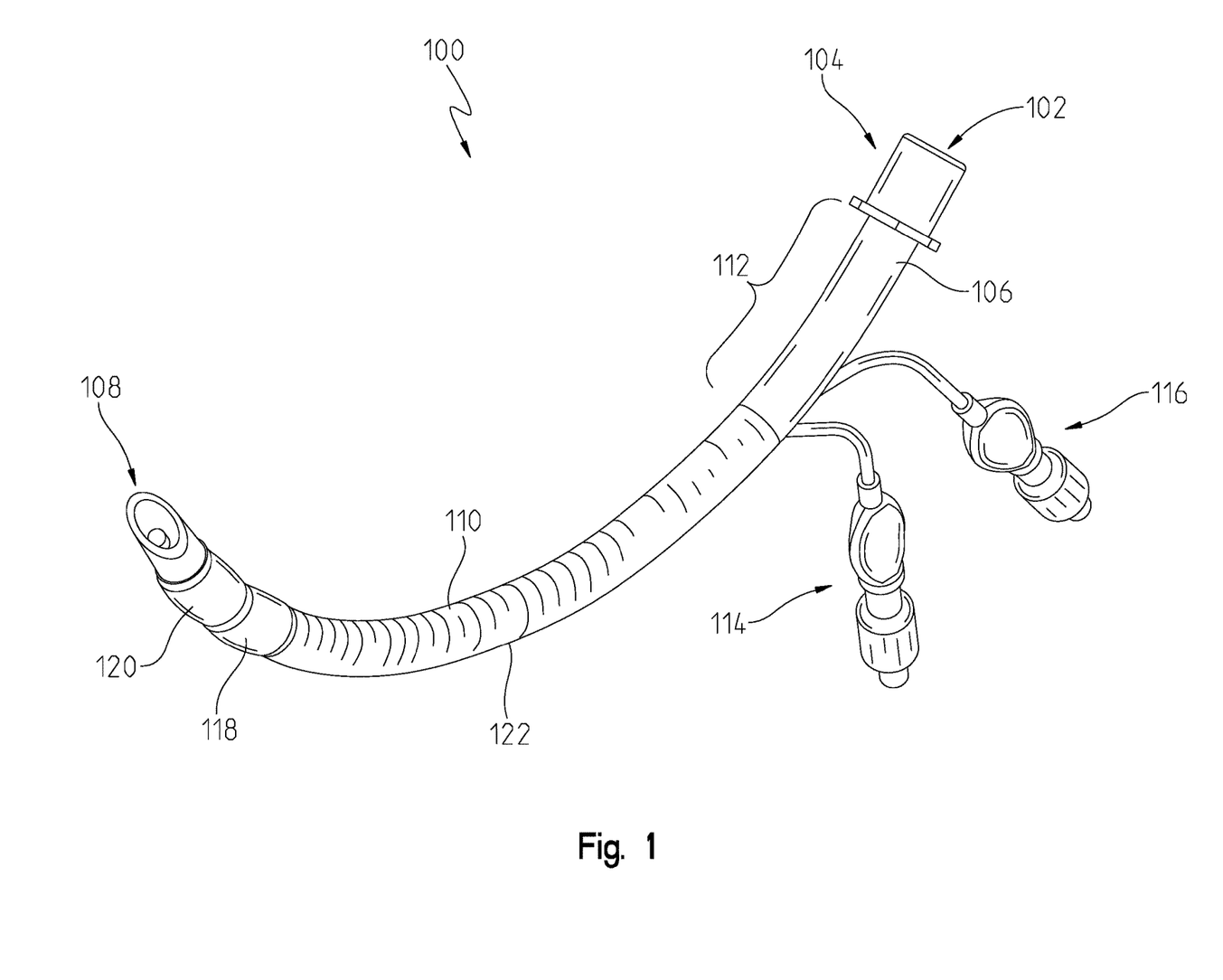
FIG. 1 is an elevated perspective view of an endotracheal tube assembly.
Figure 2:
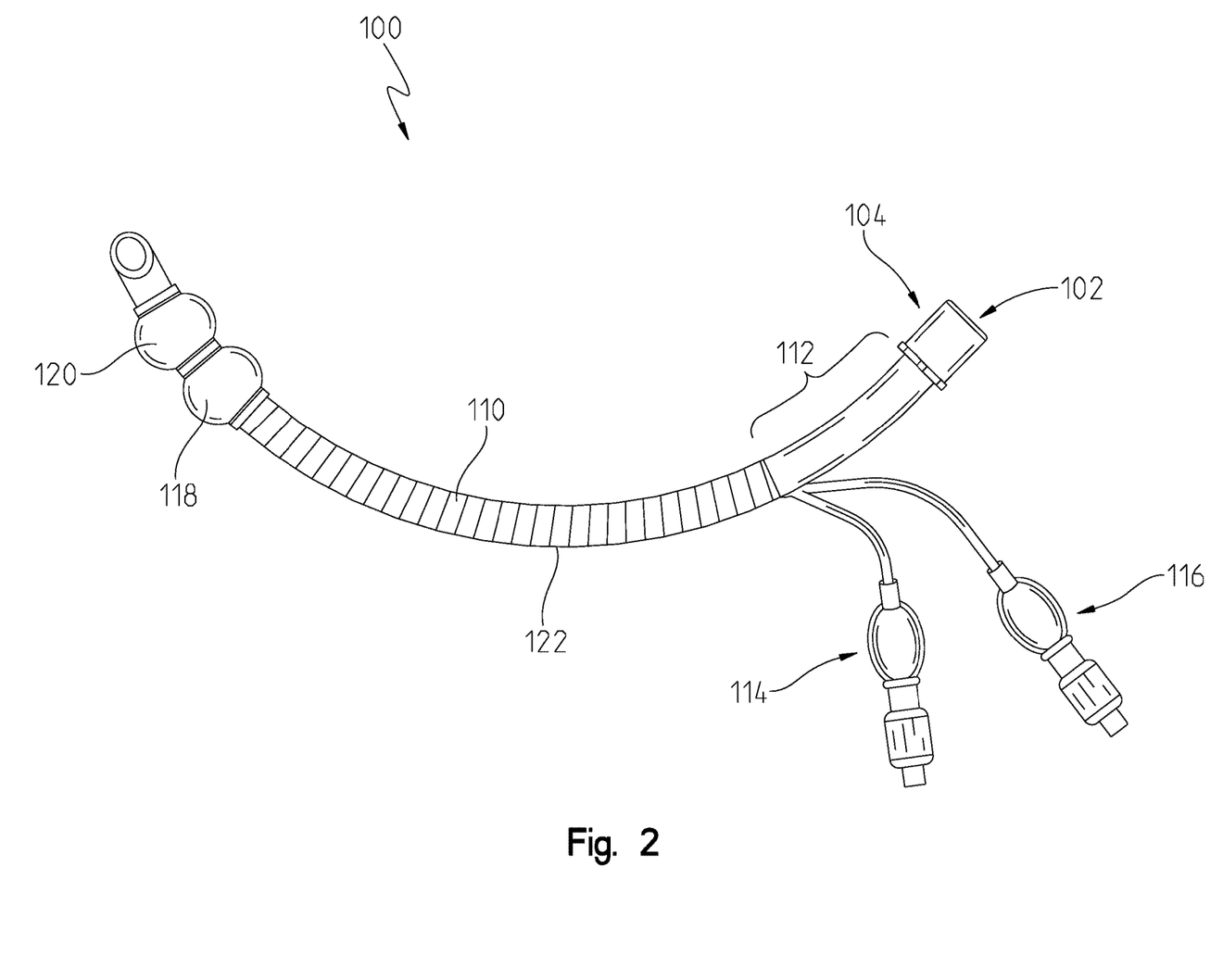
FIG. 2 is a side view of the endotracheal tube assembly of FIG. 1 with two cuffs inflated.
Figure 3:
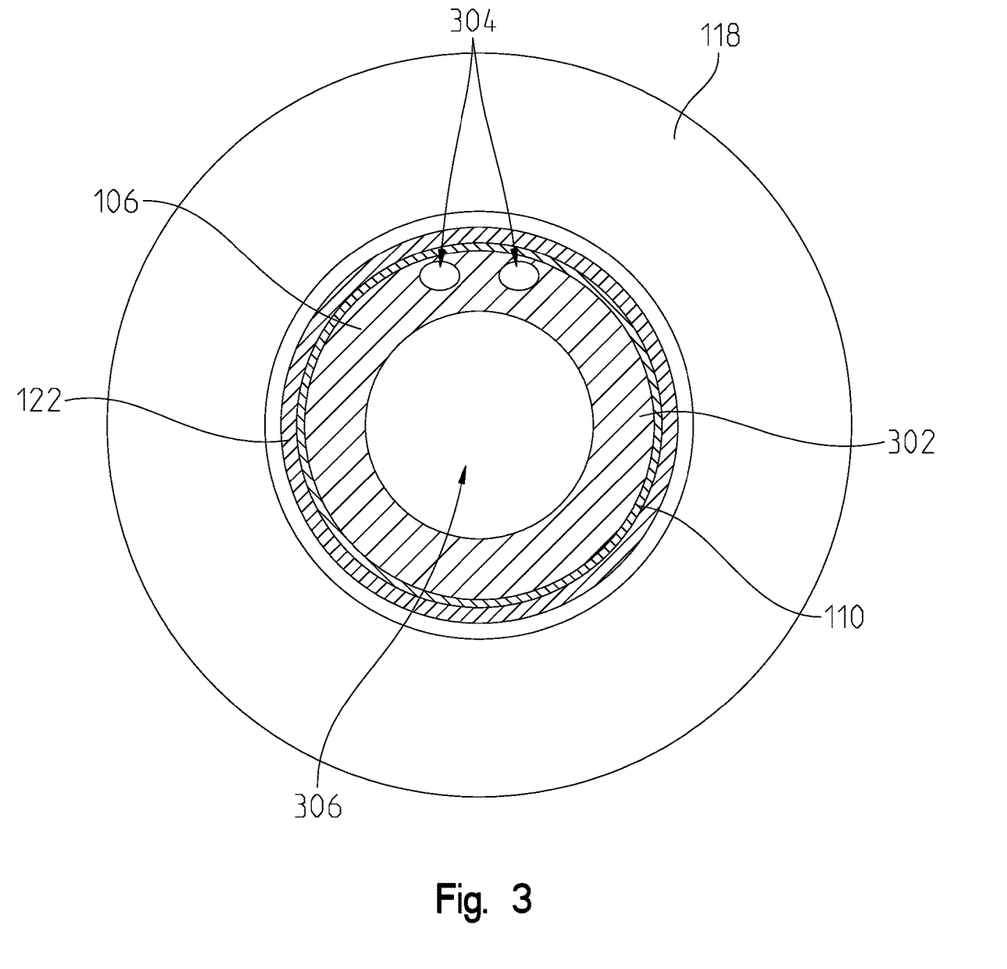
FIG. 3 is a cross-sectional view of the endotracheal tube assembly of FIG. 2.

Referring now to FIGS. 1-3, an endotracheal tube assembly 100 is illustrated isolated from a ventilator or any other medical device. The endotracheal tube assembly 100 may be formed from an airway tube 106 that has a first opening 102 on a proximal end and a second opening 108 on a distal end. The first opening 102 may have a coupler 104 coupled thereto. The coupler 104 may provide a location to fluidly couple the first opening 102 to a ventilator or other medical device to selectively provide fluid through the airway tube 106 and out the second opening 108. In one aspect of this disclosure, the airway tube 106 provides a fluidly sealed channel 306 (see FIG. 3) between the first opening 102 and the second opening 108.

The airway tube 106 may be formed of silicon or any other material that can provide a sterile, fluidly sealed inner channel 306. In one aspect of this disclosure, the airway tube 106 may be a substantially tubular structure that has an airway wall 302 (see FIG. 3). The airway wall 302 may have a thickness that is sufficient to define a first and second inflation tube passageway or lumen 304 (see FIG. 3) therein. The inflation lumen passageways 304 may provide a fluidly isolated passageway from a corresponding first and second pilot balloon 114, 116 to a proximal and distal cuff 118, 120.

Figure 4A:
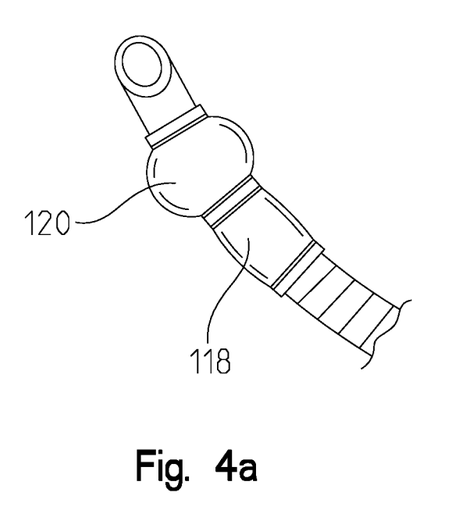
FIG. 4a is a partial side view of the endotracheal tube assembly of FIG. 1 with a distal cuff inflated.
Figure 4B:
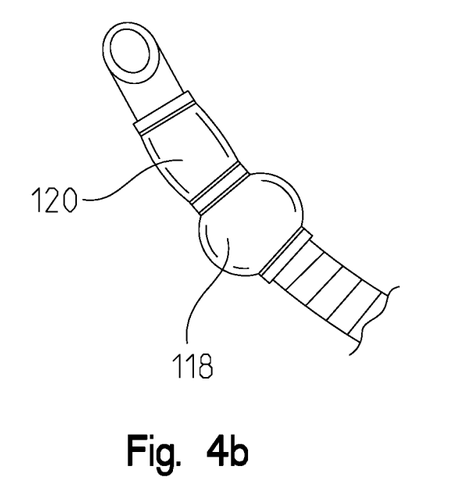
FIG. 4b is a partial side view of the endotracheal tube assembly of FIG. 2 with a proximal cuff inflated.

In one aspect of this disclosure, the first inflation pilot balloon 114 can be fluidly coupled to one of the proximal or distal cuffs 118, 120 through one of the inflation lumen passageways 304 to thereby allow the cuff to be selectively inflated (see FIGS. 4a and 4b). Similarly, the second pilot balloon 116 can be fluidly coupled to the other of the proximal or distal cuffs 118, 120 through the other of the inflation lumen passageway 304 to thereby allow the other cuff to be selectively inflated.

The airway tube 106 may also have a resistant member 110 coupled to a radially outer surface of the airway tube 106. The resistant member 110 may be any material that resist penetration by a surgical laser or any other surgical instrument that may compromise the airway tube 106. The resistant member 110 may extend a length of the airway tube 106 that corresponds with the portions of the airway tube 106 that are intended to be positioned within a patient during use. However, in one embodiment the resistant member 110 may extend substantially the entire length of the airway tube 106 less an exposed portion 112 thereof. The exposed portion 112 may be the portion of the airway tube 106 located adjacent to the coupler 104. In one example, the resistant member 110 extends from a radially inner portion of the distal cuff 120, past the proximal cuff 118, and along the airway tube 106 to the exposed portion 112. In yet another embodiment, the resistant member 110 extends between the proximal cuff 118 and the exposed portion 112.

In one aspect of this disclosure, the resistant member 110 may be formed of a material that resists penetration from a KTP laser. More specifically, a KTP laser with 400 millimeter lens microbeam coupled to a microscope may be spaced 35 centimeters from the endotracheal tube assembly 100 and deliver a focused spot of 380 micron. The KTP laser may have an angle of incidence of about ninety degrees relative to the resistance layer. Under this scenario, a laser resistant material may be any material that can resist a continuous beam for at least three minutes with the laser delivering a maximum power of about fifteen watts, continuously. More specifically, oxygen gas can be pumped through the endotracheal tube assembly 100 with the fire resistant member 110 positioned there around and the fire resistant member 110 may prevent combustion of the oxygen in the above conditions.

Alternatively or additionally, the fire resistant member 100 may be any material capable of resisting penetration by a CO2 laser. For example, an endotracheal tube assembly 100 may positioned about 35.5 centimeters from the CO2 laser wherein the CO2 laser can deliver a constant spot of about 0.38 millimeters. The CO2 laser may produce a continuous beam for at least three minutes with the CO2 laser delivering a maximum output of at least about forty to forty-five watts. In other examples, the CO2 laser may deliver a maximum output of about 60 watts. The CO2 laser may be applied multiple times at differing angles relative to the endotracheal tube assembly 100. Under this scenario, a laser resistant material may be any material that can prevent combustion of oxygen gas as it is pumped through the endotracheal tube assembly 100 while the resistant later is being exposed to the CO2 laser.

The above examples of a laser resistant material are not exhaustive. The resistant member 110 may be formed of any material that can protect the fluid flowing within the airway tube 106 from being affected by an external ignition. Accordingly, any known resistant material may be used for the resistant member 110.

In one aspect of this disclosure, the resistant member 110 is wrapped around the airway tube 106 in a helical pattern.

In this configuration, adjacent portions of the resistant member 110 partially overlap one another along the airway tube 106 to ensure the resistant member 110 fully covers the outer surface of the airway tube 106 where wrapped there around. In other words, the resistant member 110 is wrapped around the airway tube 106 to ensure that there are no sections of airway tube 106 that are not covered due to gaps in the wrapping pattern or caused by bending the airway tube 106.

While a wrapping application of the resistant member 110 is described herein, other applications are also considered. More specifically, the resistant member 110 may be formed in a sheet that is wrapped around the airway tube 106 a single time, instead of in a helical configuration. In this embodiment, the resistant member 110 may be formed from a substantially rectangular sheet that is the desired length of the resistant member 110. The sheet may then be wrapped slightly greater than three-hundred and sixty degrees around the airway tube 106 to substantially cover the outer surface. Accordingly, any known method of applying a resistant member 110 is considered herein.

Regardless of the wrapping pattern or method, the resistant member 110 may have an outer surface that is abrasive to soft tissue. Accordingly, in one aspect of this disclosure a sleeve 122 may be positioned around the radially exterior portion of the resistant member 110. The sleeve 122 may be formed from a substantially continuous material that has a smooth outer surface. In one non-exclusive example, the sleeve 122 is a tube having an inner diameter that is slightly less than the outer diameter of the resistant member 110 when positioned around the airway tube 106. In this configuration, the sleeve 122 may be stretched or otherwise expanded to be positioned around the outer surface of the resistant member 110. Once positioned there around, the sleeve 122 may return to the un-stretched size to thereby provide a radial compression to the underlying resistant member 110 compressing the resistant member 110 against the airway tube 106.

In another aspect of this disclosure, the sleeve 122 and resistant member 110 may be coupled to the underlying airway tube with an adhesive. In this aspect of the disclosure, the resistant member 110 and sleeve 122 may be positioned around the airway tube 106 as discussed herein. However, in addition to the sleeve 122 applying a compressive load to the resistant member 110 to couple the resistant member 110 and the sleeve 122 to the airway tube 106, an adhesive may be applied to the proximal and distal ends of the resistant member 110 and sleeve 122 to further couple them to the airway tube 106 with the adhesive. In one non-exclusive example, the adhesive may be a Room-Temperature-Vulcanizing ("RTV") silicone. However, any known adhesive is considered herein.

The sleeve 122 may have a wall thickness that is any suitable size. More specifically, the wall thickness may be thin enough to allow the sleeve to be stretched over the resistant member 110 but thick enough to ensure that the sleeve is not torn during manufacturing of the endotracheal tube assembly 100. In one non-exclusive example, the sleeve may be formed of silicon and have a wall thickness of between about eight thousandths of an inch and ten thousandths of an inch. However, in other embodiments the sleeve 122 may be formed of a material other than silicon. Further still, the sleeve 122 may have a wall thickness less than eight thousandths of an inch or greater than ten thousandths of an inch. Accordingly, this disclosure considers many different sizes and materials for the sleeve 122.

Referring now to FIGS. 4a and 4b, two different configurations of the cuffs 118, 120 are illustrated. In FIG. 4a, the proximal cuff 118 is illustrated deflated while the distal cuff 120 is illustrated inflated. The inflation of the proximal and distal cuffs 118, 120 may be altered by selectively providing fluid to the corresponding cuffs 118, 120 through one of the first or second pilot balloon 114, 116. In the example illustrated in FIG. 4a, the first pilot balloon 114 may be provided pressurized fluid that travels through one of the inflation lumen passageways 304 in the wall of the airway tube 106 and to an inner chamber of the distal cuff 120. Similarly, in FIG. 4b, the second pilot balloon 116 may be provided pressurized fluid that travels through the other of the inflation lumen passageways 304 in the wall of the airway tube 106 and to an inner chamber of the proximal cuff 118. Further, both the proximal and distal cuffs 118, 120 may be deflated as in FIG. 1, or inflated as in FIG. 2, depending on the amount of fluid volume and pressure provided to the inner chambers of the corresponding cuffs 118, 120 as discussed herein.

Figure 5:
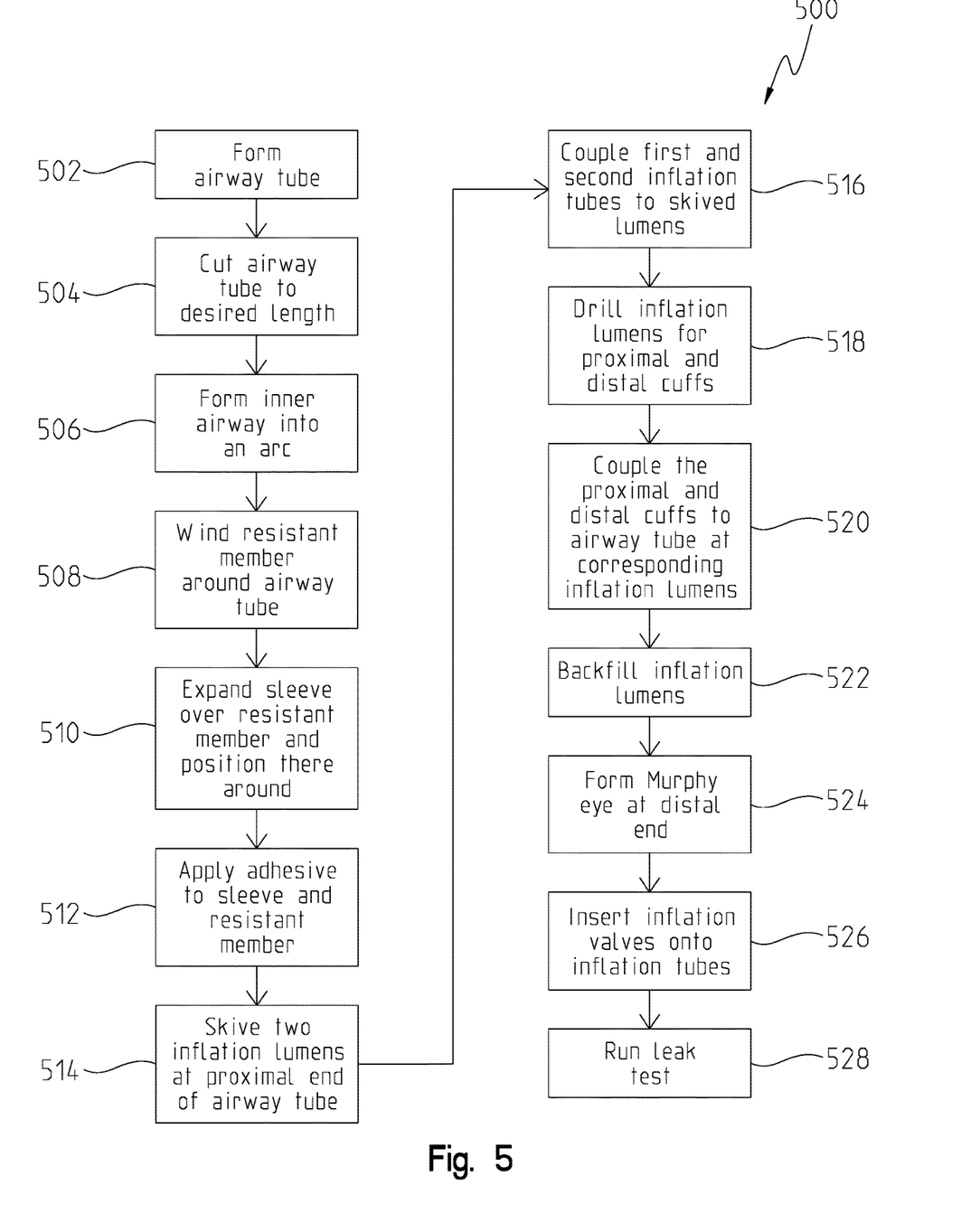
FIG. 5 is a method for manufacturing the endotracheal tube assembly of FIG. 1.

Referring now to FIG. 5, one non-exclusive example of a manufacturing method 500 is illustrated. Initially in box 502, the airway tube 106 may be formed utilizing known extrusion techniques. As part of forming the airway tube 106, the inflation lumen passageways 304 may also be formed in the wall of the airway tube 106. Next, in box 504, the airway tube 106 may be cut to any desired length depending on the desired application. In box 506, the airway tube 106 may be formed into an arc by utilizing an arc-shaped mandrel and applying a heat process thereto. In box 508, the resistant member 110 may be formed around the airway tube 106 utilizing any of the techniques described herein among others. Next, the sleeve 122 may be expanded and pulled over the resistant member 110 and the airway tube 106 in box 510. In box 512, an adhesive may be applied to the sleeve 122, the resistant member 110, and the airway tube 106 at both a proximal and distal end thereof.

In box 514, the inflation lumen passageways 304 may be skived at a proximal end of the airway tube 106. Next, in box 516 the first and second pilot balloon 114, 116 may be coupled to the corresponding skived locations of the inflation lumen passageways 304. Adhesive or the like may be utilized to ensure the first and second pilot balloon 114, 116 are fluidly coupled to the inflation lumen passageways 304. In box 518, holes may be formed through a portion of the airway tube 106 to fluidly couple the inner portion of each cuff 118, 120 to the corresponding inflation lumen passageway 304. The holes may be fluid ports that fluidly couple the corresponding inflation lumen passageway 304 to the external surface of the airway tube 106 within the cuff 118, 120. Accordingly, in box 520 the proximal and distal cuffs 118, 120 may be positioned around the corresponding fluid port and coupled to the airway tube 106. Adhesive may be used to fluidly couple the corresponding cuffs 118, 120 to the airway tube 106 to further fluidly couple the corresponding cuffs 118, 120 to the corresponding first and second pilot balloon 114, 116.

In box 522, any inflation lumen may be back filled and in box 524 a murphy eye may be formed in the distal end of the airway tube 106. Next, inflation valves may be inserted in the pilot balloon 114, 116 in box 526. Finally, in box 528 the endotracheal tube assembly 100 may be tested for leaks.

Figure 6A:
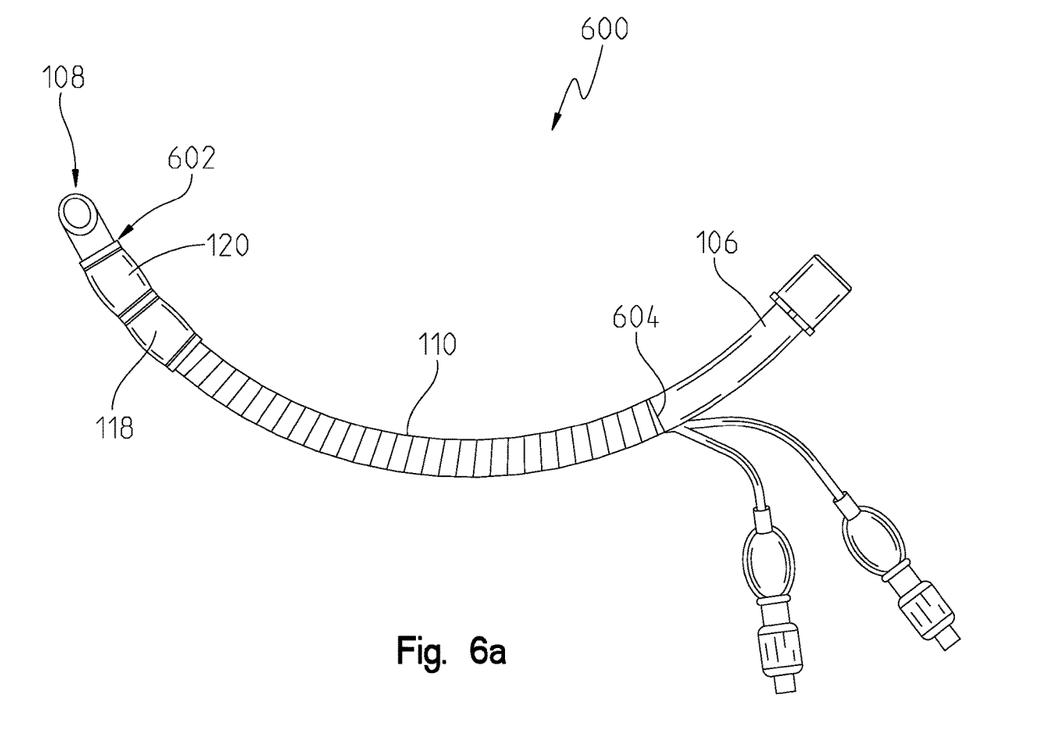
FIG. 6a is another embodiment of an endotracheal tube assembly.
Figure 6B:
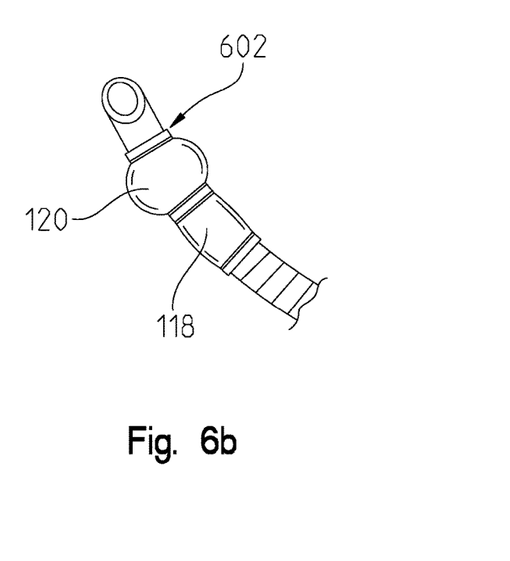
FIG. 6b is a partial side view of the endotracheal tube assembly of FIG. 6a with a distal cuff inflated.
Figure 6C:
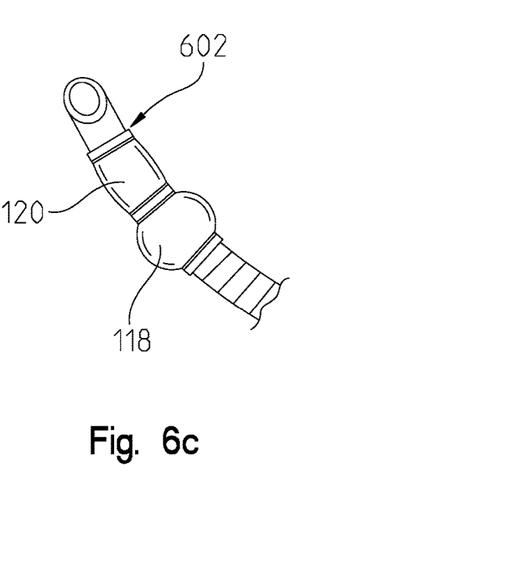
FIG. 6c is a partial side view of the endotracheal tube assembly of FIG. 6a with a proximal cuff inflated.
Figure 7:
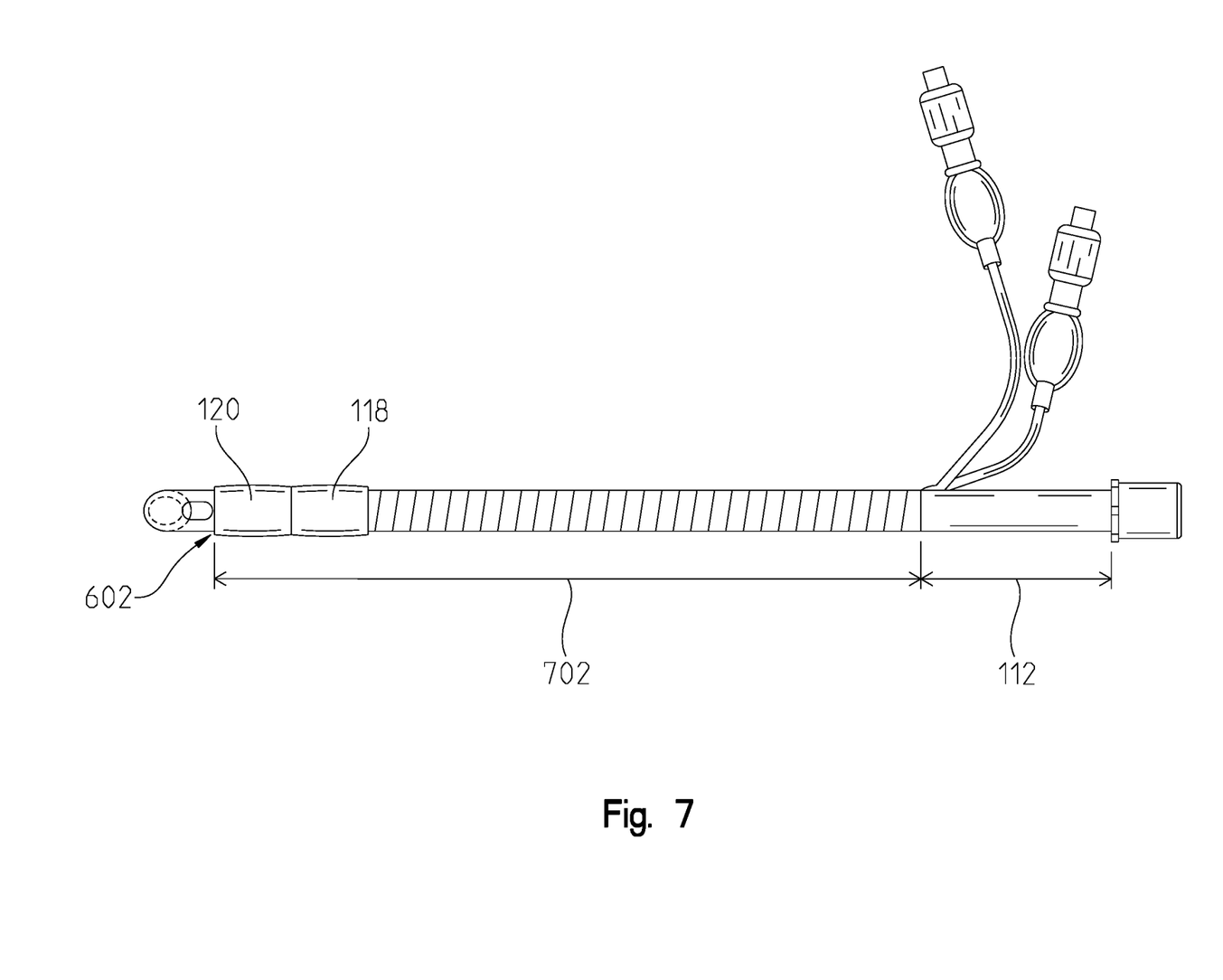
FIG. 7 is another side view of the endotracheal tube assembly of FIG. 6a in a straightened orientation.

Referring now to FIG. 6a, another embodiment of an endotracheal tube assembly 600 is illustrated. In this embodiment, the resistant member 110 may extend from a starting portion 604 of the endotracheal tube 106 to an ending portion 602 of the endotracheal tube 106. In one aspect of this disclosure, the ending portion 602 may be distal to the distal cuff 120. In other words, the resistant material 110 may extend underneath both cuffs 118, 120 towards the second opening 108. In this embodiment, the resistant material 110 may extend a resistant length 702 that is substantially the entire length of the airway tube 106 less the exposed portion 112. In this configuration, the portion of the airway tube 106 that is intended to be positioned within the patient is surrounded by the resistant material 110 up to the distal cuff 120.

In one aspect of this disclosure, the resistant material 110 is positioned radially between the cuffs 118, 120 and the inflation lumen 304. Accordingly, to fluidly couple the inner portion of the cuff 118, 120 with the corresponding inflation lumen 304 a fluid passageway must be formed through the sleeve 122, resistant material 110, and part of the airway wall 302. One aspect of this disclosure is a method of forming this fluid connection while ensuring the passageway from the inflation lumen 304 through the airway wall 302, resistant material 110, and sleeve 122 is fluidly sealed.

Figure 8:
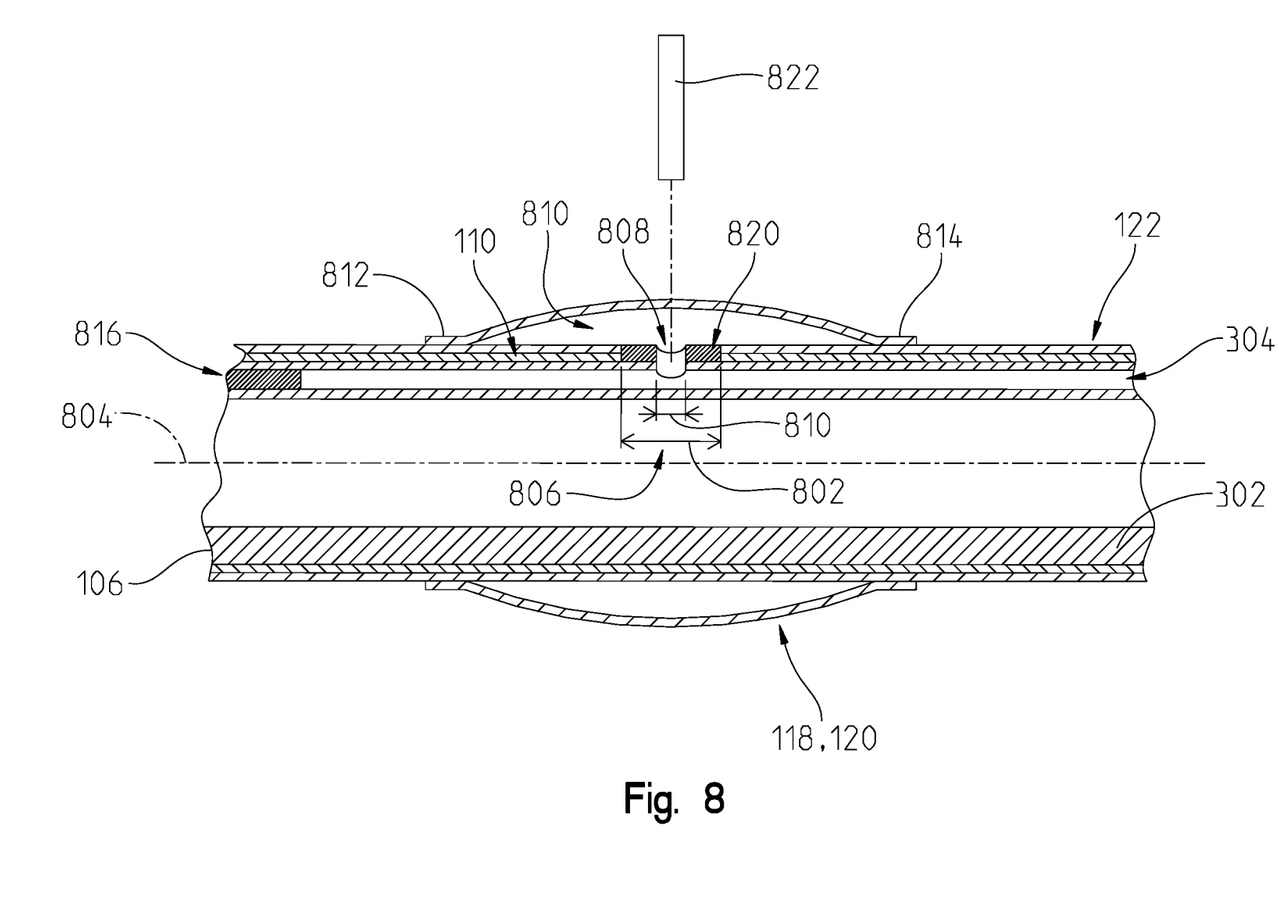
Figure 9:
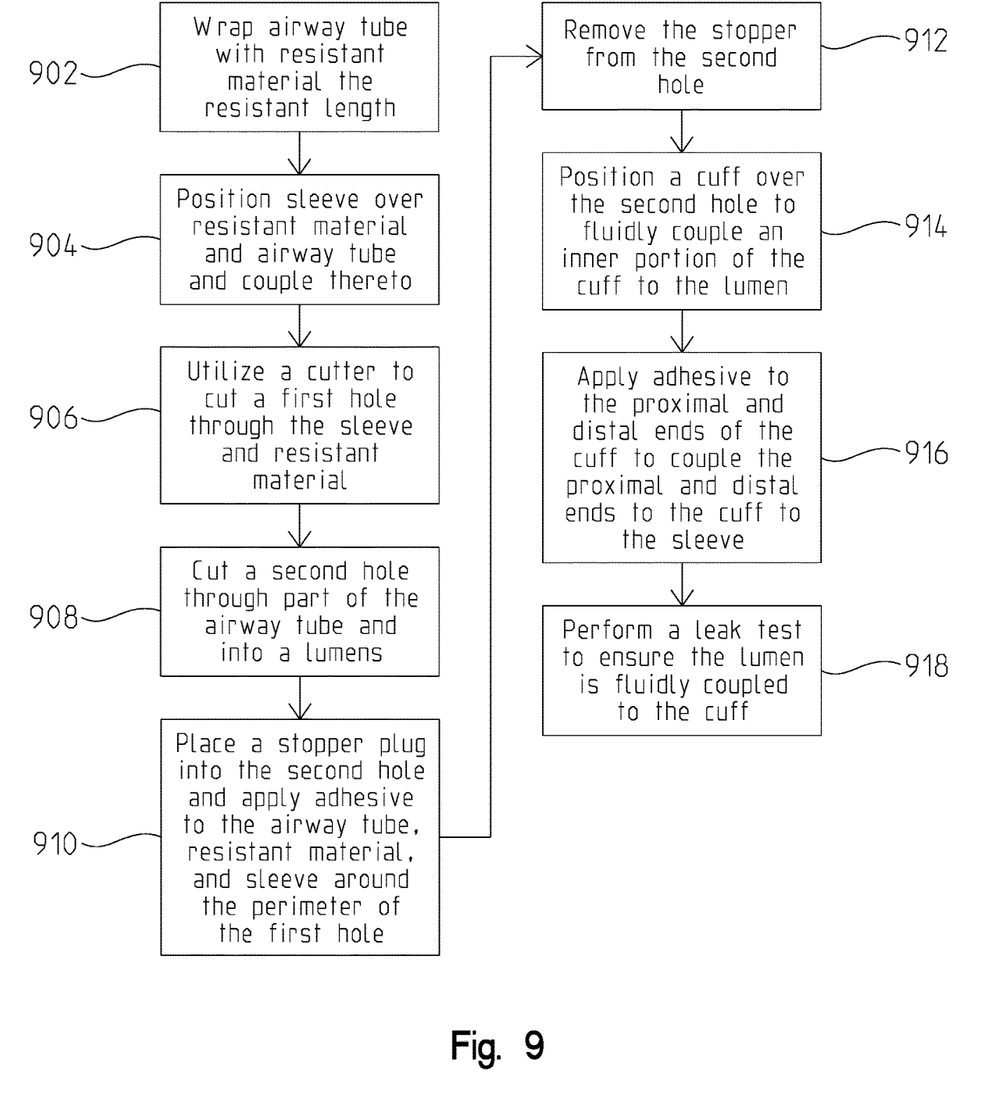

Referring now to FIGS. 8 and 9, one non-exclusive method for fluidly coupling a cuff 118, 120 to the corresponding inflation lumen 304 is described. In box 902, the airway tube 106 may be wrapped with the resistant material 110 as discussed herein. In box 902, the resistant material 110 is wrapped to be positioned axially along the airway tube 106 passed the proximal cuff 118 and at least partially into the distal cuff 120. In one aspect of this disclosure, the resistant material 110 is wrapped to extend along the airway tube 106 axially past both the proximal and distal cuffs 118, 120. Next in box 904, the sleeve 122 is positioned over the resistant material 110 and coupled to the airway tube 106 and resistant material 110 as discussed herein.

In box 906, a cutter having a first diameter 802 is used to cut a first hole 806 through the sleeve 122 and the resistant material 110 at a location radially outward of a corresponding inflation lumen 304. The first hole 806 may be radially outward of the inflation lumen 304 relative to an airway axis 804 defined longitudinally through a center portion of the airway tube 106. In one aspect of this disclosure, the cutter is not advanced substantially radially into the airway wall 302 of the airway tube 106 but rather is only advanced far enough to cut holes through the sleeve 122 and the resistant material 110. While a portion of the airway tube 106 may be slightly contacted when cutting the first hole 806, the cutter for the first hole 806 does not advance into the inflation lumen 304. In other words, the cutter only advances far enough radially inward to cut the first hole 806 in the sleeve 122 and the resistant member 110. All portions of the sleeve 122 and resistant material 110 are removed from the first hole 806 to expose a radially outer surface of the airway tube 106.

Next, in box 908, a second hole 808 may be cut partially through the airway tube 106 into the underlying inflation lumen 304. The second hole 808 may be aligned to be substantially coaxial with the first hole 806. In one non-exclusive embodiment, the second hole 808 may have a second diameter 810 that is slightly less than the first diameter 802. The second hole 808 is only defined partially through the airway wall 302 of the airway tube 106 in order to provide an outlet (the second hole 808) for the underlying inflation lumen 304 to be routed radially outwardly from the airway tube 106. As discussed herein, ultimately one of the cuffs 118, 120 will be positioned along the outlet to fluidly couple the inflation lumen 304 to an inner chamber of the corresponding cuff 118, 120.

In box 910, a stopper plug 822 may be positioned through the second hole 808 to substantially fill the second hole 808. The stopper plug 822 may have a diameter that is the same or slightly greater than the second diameter 810 to substantially fill the second hole 808 when placed therein. Further, the stopper plug 822 may extend radially away from the sleeve 122 to define an annular channel 820 around the stopper plug 822. The annular channel 820 may be defined by the stopper plug 822, outer surface of the airway tube 106 between the first and second hole, the resistant member 110 along the perimeter of the first hole 806, and the sleeve 122 along the perimeter of the first hole 806. In box 910, an adhesive can be applied into the annular channel 820 while the stopper plug 822 is positioned through the second hole 808. By placing the adhesive in the annular channel 820, any gaps between the sleeve 122, resistant member 110, and airway tube 106 may be substantially filled with adhesive to ensure no fluid can pass through the first hole 806 to occupy the space between the sleeve 122 and the outer surface of the airway tube 106. In other words, applying adhesive to the annular channel 820 prevents fluid from bleeding into the resistant material 110 layer when the corresponding cuff 118, 120 is inflated.

The adhesive may be any known adhesive and in one non-exclusive embodiment is RTV silicone. Further, the plug may be formed from a material that resists adhesion by the adhesive. In one non-exclusive example, the plug may be formed of a Teflon material. However, any known adhesive and plug material may be used, and this disclosure considers all known adhesives and plug materials.

Referring now to box 912, the stopper plug 822 may be removed from the second hole 808 after the adhesive has at least partially cured. As discussed herein, the stopper plug 822 may be formed of a material that substantially resists adhesion to the adhesive. Accordingly, after the adhesive has at least partially cured, the plug may be removed from the second hole 808. Further, since the adhesive is at least partially cured, the second hole 808 may remain defined partially through the airway tube 106 to fluidly couple the inflation lumen 304 to the outer portion of the sleeve 122.

Next, in box 914 the corresponding cuff 118, 120 may be positioned around the sleeve 122 at a location axially aligned with the second hole 808. More specifically, the cuff 118, 120 may be aligned with the second hole 808 so the second hole 808 fluidly couples a corresponding inflation lumen 304 with a cavity 818 of the cuff 118, 120. In box 916, each cuff 118, 120 may be coupled to the radially outer surface of the sleeve 122 at a proximal and distal end 812, 814 with adhesive. The cavity 818 is formed between the inner surface of the cuff 118, 120 and the outer surface of the sleeve 122 between the proximal and distal ends 812, 814 of the cuff 118, 120. Further, a cap 816 may be formed at a distal end of the inflation lumen 304 with adhesive to prevent fluid flow out the distal end. Accordingly, fluid provided through the inflation lumen 304 passes through the second hole 808 and into the cavity 818 to thereby expand the cuff 118, 120 under certain pressure and volume conditions.

Finally, in box 918 a leak test may be executed to ensure that the inflation lumen 304 is fluidly coupled to the cuff 118, 120. More specifically, fluid may be provided to the inflation lumen 304 at an established fluid pressure to fill the cavity 818. The fluid may be provided at a test pressure and monitored for a period of time to ensure that the test pressure does not drop. A drop in test pressure may indicate a leak between the inflation lumen 304 and the cuff 118, 120. As discussed herein, one aspect of the leak test may be to ensure that fluid is not passing through the perimeter of the first hole 806 and into the space between the sleeve 122 and the airway tube 106. In other words, one aspect of the leak test is to ensure that the adhesive applied to the annular channel 820 is properly sealing the sleeve 122, resistant member 110, and airway tube 106 about the perimeter of the first hole 806.

While FIGS. 8 and 9 illustrate and describe a method for fluidly coupling a single cuff to an inflation lumen, this disclosure contemplates utilizing substantially the same methodology discussed herein to fluidly couple two or more cuffs thereto as well. More specifically as illustrated in FIG. 3, two inflation lumen 304 may be defined in the airway wall 302. In this embodiment, the methods discussed herein can be implemented to couple the proximal cuff 118 to a first inflation lumen and then couple the distal cuff 120 to a second inflation lumen. In this configuration, the first and second holes 806, 808 would be located along different portions of the airway tube 106 to thereby fluidly couple the corresponding cuff 118, 120 to one of the first or second inflation lumen. Accordingly, the teachings of this disclosure may be applied to endotracheal tubes with any number of cuffs.

In use, the endotracheal tube assembly 100 described herein may be utilized for procedures that may expose the endotracheal tube assembly 100 to a surgical laser or the like. In these types of procedures, the endotracheal tube assembly 100 may be inserted partially past the vocal chords and into the trachea of a patient without abrasively contacting the soft tissue. The cuff or cuffs may be inflated to fluidly seal the endotracheal tube assembly 100 to the walls of the trachea. Then, the physician can perform the procedure utilizing a surgical laser or the like while fluid is passed through the endotracheal tube assembly 100 and into the patient.

If the physician unintentionally contacts the endotracheal tube assembly 100 with the surgical laser, the resistant member 110 may substantially reflect or otherwise block the laser from entering the fluid passageway of the airway tube 106. Once the procedure is complete, the physician may deflate the cuff or cuffs and remove the endotracheal tube assembly 100 from the patient without abrasively contacting the trachea or vocal chords. More specifically, the sleeve 122 and cuffs 118, 120 may cover substantially the entire outer surface of the resistant member 110 to ensure the endotracheal tube assembly 100 can be smoothly inserted and removed from the patient.

As discussed herein, the resistant member 110 may extend axially along the airway tube 106 past the proximal cuff and partially into, or past, the distal cuff. By extending the resistant member 110 substantially the entire length of the airway tube 106, the physician can utilize a surgical laser or the like along portion of the patient that are adjacent to the cuffs 118, 120. More specifically, if the physician inadvertently redirects the surgical laser into the cuffs 118, 120 and toward the airway tube 106, the resistant member 110 may still substantially prevent the surgical laser from passing into the airway tube 106.

While exemplary embodiments incorporating the principles of the present disclosure have been described herein, the present disclosure is not limited to such embodiments. Instead, this application is intended to cover any variations, uses, or adaptations of the disclosure using its general principles. Further, this application is intended to cover such departures from the present disclosure as come within known or customary practice in the art to which this disclosure pertains.

The invention claimed is:

1. An endotracheal tube assembly, comprising:
    an airway tube forming a fluid channel from a first opening to a second opening and defining a tube wall;
    a resistant member formed around a portion of the airway tube;
    a sleeve formed around the resistant member; and
    a first cuff formed along the airway tube proximate to the second opening;
    wherein, the sleeve is formed of a single material having a substantially smooth outer surface,
    wherein the sleeve and the resistant member have a first hole there through at a location proximate to a first inflation lumen and the airway tube has a second hole partially there through, the second hole aligned with the first hole;
    wherein an adhesive fluidly seals a perimeter of the first hole to fluidly couple the first cuff to the first inflation lumen such that fluid from the first inflation lumen is prevented from entering a space between the airway tube and the sleeve.

2. The endotracheal tube assembly of claim 1, further comprising a second cuff formed along the airway adjacent to the first cuff.

3. The endotracheal tube assembly of claim 2, further comprising the first inflation lumen defined at least partially within the tube wall and fluidly coupled to the first cuff and a second inflation lumen defined at least partially within the tube wall and fluidly coupled to the second cuff.

4. The endotracheal tube assembly of claim 3, further wherein the first cuff and second cuff are inflatable independent of one another.

5. The endotracheal tube assembly of claim 1, further wherein the resistant member is positioned radially inside of at least a portion of the first cuff.

6. The endotracheal tube assembly of claim 1, further wherein the resistant member is wrapped around the airway tube and the sleeve radially compresses the resistant member towards the airway tube.

7. The endotracheal tube assembly of claim 6, further wherein the resistant member and the sleeve are adhesively coupled to the airway tube at a proximal and a distal end of both the resistant member and the sleeve.

8. A method for manufacturing an endotracheal tube, comprising:
    forming an airway tube with at least two inflation lumen passageways defined in a wall of the airway tube;
    winding a resistant member around an outer portion of the airway tube;
    expanding a sleeve and positioning the sleeve around the resistant member;
    allowing the sleeve to contract to thereby compress the resistant member against the airway tube;
    cutting a first hole through the sleeve and the resistant member at a location proximate to one of the at least two inflation lumen passageways;
    cutting a second hole partially through the airway tube, the second hole aligned with the first hole;
    applying an adhesive along a perimeter of the first hole; and
    coupling a proximal and distal cuff to the airway tube and fluidly coupling one of the two inflation lumen passageways to one of the proximal and distal cuff through the second hole.

9. The method of claim 8, further comprising applying adhesive to a proximal and distal end of both the sleeve and resistant member to thereby adhesively couple the sleeve and resistant member to the airway tube.

10. A method of coupling a cuff to an inflation lumen for an endotracheal tube, comprising:
- providing an endotracheal tube having an inflation lumen defined therein, a resistant material positioned around at least a portion of the endotracheal tube, and a sleeve positioned around at least a portion of the resistant material;
- cutting a first hole through the sleeve and the resistant material at a location proximate to the inflation lumen;
- cutting a second hole partially through the endotracheal tube, the second hole aligned with the first hole;
- inserting a stopper into the second hole and applying an adhesive around the stopper along a perimeter of the first hole;
- removing the stopper and coupling the cuff along the endotracheal tube to fluidly couple the cuff to the inflation lumen through the second hole.

11. The method according to claim 10, comprising wrapping the resistant material around the endotracheal tube and positioning the sleeve over the resistant material and coupling the sleeve and the resistant material to the endotracheal tube by applying an adhesive to the resistant material and the sleeve at a proximal and distal end of both the resistant material and the sleeve.

12. The method of claim 10, wherein the first hole is cut by a cutter having a first diameter and all portions of the sleeve and the resistant material are removed from the first hole.

13. The method of claim 10, wherein the second hole is cut partially through the airway tube into the underlying inflation lumen.

14. The method of claim 10, wherein the second hole is aligned coaxial with the first hole.

15. The method of claim 12, wherein the second hole has a second diameter which is less than the first diameter.

16. The method of claim 15, wherein the stopper plug has a diameter which is the same or greater than the second diameter and is configured to substantially fill the second hole when placed therein.

17. The method of claim 16, wherein the adhesive is applied into an annular channel defined by the stopper plug, the outer surface of the airway tube between the first hole and the second hole, the resistant material along the perimeter of the first hole and the sleeve around the perimeter of the first hole.

18. The method of claim 10, wherein the stopper plug is removed from the second hole after the adhesive has at least partially cured.

19. The method of claim 10, wherein the stopper plug is formed from a material that resists adhesion by the adhesive.

20. The method of claim 10, wherein a cap is formed at a distal end of the inflation lumen with adhesive to prevent fluid flow out the distal end.

21. The method of claim 10, wherein a leak test is executed to ensure that the inflation lumen is fluidly coupled to the cuff.

\* \* \* \* \*